US00PP25104P2

(12) United States Plant Patent
Kolster

(10) Patent No.: US PP25,104 P2
(45) Date of Patent: Nov. 25, 2014

(54) ***HYDRANGEA* PLANT NAMED 'KOLMARU'**

(50) Latin Name: *Hydrangea macrophylla*
Varietal Denomination: Kolmaru

(71) Applicant: Peter R. Kolster, Boskoop (NL)

(72) Inventor: Peter R. Kolster, Boskoop (NL)

(73) Assignee: Kolster Holding, B.V., Boskoop (NL)

( * ) Notice: Subject to any disclaimer, the term of this patent is extended or adjusted under 35 U.S.C. 154(b) by 167 days.

(21) Appl. No.: 13/694,024

(22) Filed: Oct. 20, 2012

(51) Int. Cl.
*A01H 5/00* (2006.01)

(52) U.S. Cl.
USPC ..... Plt./250

(58) Field of Classification Search
CPC ..... A01H 5/02; A01H 5/00; A01H 1/02
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Kolmaru', characterized by its upright and somewhat outwardly spreading plant habit; strong erect stems; glossy dark green-colored leaves; freely flowering habit; and large flattened globular mophead-type inflorescences with red purple-colored sterile flowers.

3 Drawing Sheets

Botanical designation: *Hydrangea macrophylla.*
Cultivar denomination: 'KOLMARU'.

BACKGROUND OF THE INVENTION

The present invention relates to a new and distinct cultivar of *Hydrangea* plant, botanically known as *Hydrangea macrophylla* and hereinafter referred to by the name 'Kolmaru'.

The new *Hydrangea* plant is a product of a planned breeding program conducted by the Inventor in Boskoop, The Netherlands. The objective of the breeding program is to create new mophead-type *Hydrangea* plants that can be used as cut flower types and have red purple-colored sterile flowers.

The new *Hydrangea* plant originated from a cross-pollination conducted by the Inventor in May, 2006 in Boskoop, The Netherlands of *Hydrangea macrophylla* 'Glowing Alps', not patented, as the female, or seed parent with a proprietary selection of *Hydrangea macrophylla* identified as code number 06-099-01, not patented, as the male, or pollen, parent. The new *Hydrangea* plant was discovered and selected by the Inventor as a single flowering plant within the progeny of the stated cross-pollination in a controlled greenhouse environment in Boskoop, The Netherlands in May, 2008.

Asexual reproduction of the new *Hydrangea* plant by vegetative cuttings in a controlled greenhouse environment in Boskoop, The Netherlands since July, 2008 has shown that the unique features of this new *Hydrangea* plant are stable and reproduced true to type in successive generations.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Kolmaru'.

These characteristics in combination distinguish 'Kolmaru' as a new and distinct *Hydrangea* plant:

1. Upright and somewhat outwardly spreading plant habit.
2. Strong erect stems.
3. Glossy dark green-colored leaves.
4. Freely flowering habit.
5. Large flattened globular mophead-type inflorescences with red purple-colored sterile flowers.

Plants of the new *Hydrangea* differ primarily from plants of the female parent, 'Glowing Alps', in the following characteristics:

1. Leaves of plants of the new *Hydrangea* are smaller and darker green in color than leaves of plants of 'Glowing Alps'.
2. Plants of the new *Hydrangea* and 'Glowing Alps' differ in sterile flower color as sterile flowers of plants of 'Glowing Alps' are dark pink in color.

Plants of the new *Hydrangea* differ primarily from plants of the male parent selection in the following characteristics:

1. Plants of the new *Hydrangea* are more freely flowering than plants of the male parent selection.
2. Plants of the new *Hydrangea* and the male parent selection differ in sterile flower color as sterile flowers of plants of the male parent selection are dark pink in color.

Plants of the new *Hydrangea* can be compared to plants of *Hydrangea macrophylla* 'Kolmgarip', not patented. Plants of the new *Hydrangea* differ primarily from plants of 'Kolmgarip' in the following characteristics:

1. Leaves of plants of the new *Hydrangea* are smaller and darker green in color than leaves of plants of 'Kolmgarip'.
2. Plants of the new *Hydrangea* and 'Kolmgarip' differ in sterile flower color as plants of 'Kolmgarip' have deep pink-colored sterile flowers.

Plants of the new *Hydrangea* can also be compared to plants of *Hydrangea macrophylla* 'Horo', not patented. Plants of the new *Hydrangea* differ primarily from plants of 'Horo' in the following characteristics:

1. Leaves of plants of the new *Hydrangea* are smaller and darker green in color than leaves of plants of 'Horo'.
2. Plants of the new *Hydrangea* are more freely flowering than plants of 'Horo'.
3. Plants of the new *Hydrangea* and 'Horo' differ in sterile flower color as plants of 'Horo' deep pink-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color value cited in the detailed botanical description which accurately describe the colors of the new *Hydrangea* plant.

The photograph on the first sheet comprises a side perspective view of a typical plant of 'Kolmaru' grown in a container.

The photograph on the second sheet is a close-up view of the upper surface of a typical leaf of 'Kolmaru'.

The photograph on the third is a close-up view of a typical inflorescence of 'Kolmaru'.

DETAILED BOTANICAL DESCRIPTION

Plants used in the aforementioned photographs and in the following description were grown during the spring in three-liter (28-cm) containers in a glass-covered greenhouse in Boskoop, The Netherlands and under cultural conditions which closely approximate commercial *Hydrangea* production. During the production of the plants, day temperatures ranged from 15° C. to 20° C. and night temperatures ranged from 14° C. to 15° C. Plants of the new *Hydrangea* were one year old when the photographs and description were taken. In the following description, color references are made to The Royal Horticultural Society Colour Chart, 2007 Edition, except where general terms of ordinary dictionary significance are used.

Botanical description: *Hydrangea macrophylla* 'Kolmaru'.

Parentage:

*Female, or seed, parent.*—*Hydrangea macrophylla* 'Glowing Alps', not patented.

*Male, or pollen, parent.*—Proprietary selection of *Hydrangea macrophylla* identified as code number 06-099-01, not patented.

Propagation:

*Method.*—By softwood cuttings.

*Time to initiate roots, summer.*—About three weeks at temperatures ranging from 15° C. to 25° C.

*Time to initiate roots, winter.*—About five weeks at temperatures ranging from 10° C. to 20° C.

*Time to produce a rooted young plant, summer.*—About six weeks at temperatures ranging from 15° C. to 25° C.

*Time to produce a rooted young plant, winter.*—About ten weeks at temperatures ranging from 10° C. to 20° C.

*Root description.*—Medium in thickness, fibrous; cream in color.

*Rooting habit.*—Moderately freely branching; medium density.

Plant description:

*Plant and growth habit.*—Upright plant habit; broad inverted triangle; strong erect stems; about eight lateral branches develop per plant, pinching enhances lateral branch development; moderately vigorous growth habit.

*Plant height.*—About 37 cm.

*Plant diameter or area of spread.*—About 41.1 cm.

*Lateral branches.*—Length: About 22.3 cm. Diameter: About 6 mm. Internode length: About 4.7 cm. Texture: Smooth, glabrous. Angle: Mostly erect to about 45° from vertical. Strength: Strong. Color, developing: Close to 143B; at the nodes, close to between 183A to 187A. Color, fully developed: Close to N199A to N199B. Lenticels: Density: About one per $cm^2$. Length: About 2 mm. Width: About 1 mm. Color: Close to 183A.

Foliage description:

*Arrangement.*—Opposite, simple.

*Length.*—About 9.1 cm.

*Width.*—About 7.1 cm.

*Shape.*—Broadly elliptic to broadly obovate to broadly ovate.

*Apex.*—Apiculate.

*Base.*—Short attenuate.

*Margin.*—Serrate.

*Texture, upper surface.*—Smooth to slightly rugose; glabrous.

*Texture, lower surface.*—Smooth; mostly glabrous with sparse pubescent along veins.

*Luster, upper surface.*—Glossy.

*Luster, lower surface.*—Slightly glossy.

*Venation pattern.*—Pinnate.

*Color.*—Developing leaves, upper surface: Between N137A and 141A. Developing leaves, lower surface: Between 143A and 146A to 146B. Fully expanded leaves, upper surface: Darker than between N137A and 147A; venation, close to 144A. Fully expanded leaves, lower surface: Close to 138B; venation, close to 144B to 144C.

*Petiole.*—Length: About 1.2 cm. Diameter: About 3.5 mm. Texture, upper and lower surfaces: Smooth, glabrous. Luster, upper and lower surfaces: Moderately glossy. Color, upper and lower surfaces: Close to 144A.

Flower description:

*Flower type and habit.*—Single fertile and sterile flowers arranged on large mophead-type panicles; panicles terminal and flattened globular in shape; sterile flowers face upright to outwardly and fertile flowers face mostly upright.

*Fragrance.*—None detected.

*Natural flowering season.*—Continuous flowering from late spring to late summer in The Netherlands.

*Flower longevity, fertile flowers.*—About one week on the plant; fertile flowers not persistent.

*Flower longevity, sterile flowers.*—About six weeks on the plant; sterile flowers persistent.

*Quantity of flowers.*—Freely flowering habit; about 24 fertile flowers and about 86 sterile flowers per panicle.

*Panicle height.*—About 10.2 cm.

*Panicle diameter.*—About 17.1 cm.

*Flower buds, fertile flowers.*—Length: About 3 mm. Diameter: About 3 mm. Shape: Broadly obovate. Color: Close to 63C; towards the base, close to 144C.

*Flower buds, sterile flowers.*—Length: About 1 cm. Diameter: About 5 mm. Shape: Ovate. Color: Close to 144B and 145A.

*Fertile flowers*.—Diameter: About 7 mm. Depth: About 3.5 mm. Shape: Rotate. Petals: Quantity per flower: Five in a single whorl. Length: About 3 mm. Width: About 1.5 mm. Shape: Broadly ovate, concave. Apex: Broadly acute. Base: Cuneate. Margin: Entire. Texture, upper and lower surfaces: Smooth, glabrous. Color: When opening and fully opened, upper surface: Close to 62A; spots, close to 63B. When opening and fully opened, lower surface: Close to 63B to 63C. Sepals: Quantity per flower: Five in a single whorl. Length: About 1.5 mm. Width: About 1 mm. Shape: Ovate. Apex: Acute. Base: Broadly cuneate. Margin: Entire. Texture, upper and lower surfaces: Smooth, glabrous. Color: When opening, upper and lower surfaces: Close to 144C. Fully opened, upper and lower surfaces: Close to 144C. Pedicels: Length: About 4 mm. Diameter: About 1 mm. Strength: Moderately strong. Angle: About 15° from vertical. Texture: Smooth, glabrous. Color: Close to 59D; spots, close to 59C. Reproductive organs: Stamens: Quantity per flower: Ten. Filament length: About 1.5 mm. Filament color: Close to 62D and N155B. Anther shape: Broadly reniform. Anther length: About 0.5 mm. Anther color: Close to 62C to 62D and 155A. Pollen amount: Scarce. Pollen color: Close to 156C to 156D. Pistils: Quantity per flower: Three. Pistil length: About 1 mm. Stigma shape: Club-shaped. Stigma color: Close to N155B. Style length: About 0.5 mm. Style color: Close to 62D. Ovary color: Close to 145A to 145B.

*Sterile flowers*.—Shape: Rotate, cruciform. Diameter: About 4.6 cm. Depth (height): About 1.5 cm. Petals: Quantity per flower: Four in a single whorl. Length: About 2.5 mm. Width: About 1.5 mm. Shape: Broadly ovate, concave. Apex: Broadly acute. Base: Cuneate. Margin: Entire. Texture, upper and lower surfaces: Smooth, glabrous. Color: When opening and fully opened, upper surface: Close to 62A; spots, close to 63B. When opening and fully opened, lower surface: Close to 63B to 63C. Sepals: Quantity per flower: Four in a single whorl. Length: About 2.4 cm. Width: About 2.9 cm. Shape: Deltoid to broadly rhomboidal. Apex: Bluntly acute to rounded. Base: Cuneate. Margin: Entire or serrate. Texture, upper and lower surfaces: Smooth, glabrous. Color: When opening, upper surface: Close to 53D; towards the base, close to 145C. When opening, lower surface: Between 53D and 59D; towards the base, close to 145C. Fully opened, upper surface: Close to 60A irregularly and sparsely marbled with close to 187B; with development color becomes closer to between N186C and 203B with base, close to 59C. Fully opened, lower surface: Close to 186B; with development color becomes closer to 148B with close, close to 59D. Pedicels: Length: About 3.1 cm. Diameter: About 1.5 mm. Strength: Strong. Angle: About 32.5° from stem. Texture: Moderately pubescent. Color: Close to 59D. Reproductive organs: Stamens: Quantity per flower: Eight. Filament length: About 1.5 mm. Filament color: Close to between 62D and N155B. Anther shape: Broadly reniform. Anther length: About 0.5 mm. Anther color: Between 62C to 62D and 155A. Pollen amount: Scarce. Pollen color: Close to 156C to 156D. Pistils: Quantity per flower: Two. Pistil length: About 1 mm. Stigma shape: Club-shaped. Stigma color: Close to N155B. Style length: About 0.5 mm. Style color: Close to 62D. Ovary color: Close to 145A to 145B. Fruits and seeds: Fruit and seed development have not been observed on plants of the new *Hydrangea*.

Disease & pest resistance: Plants of the new *Hydrangea* have not been observed to be resistant to pathogens or pests common to *Hydrangea* plants.

Temperature tolerance: Plants of the new *Hydrangea* have been shown to be tolerant to temperatures ranging from about −20° C. to about 40° C.

It is claimed:

1. A new and distinct *Hydrangea* plant named 'Kolmaru' as illustrated and described.

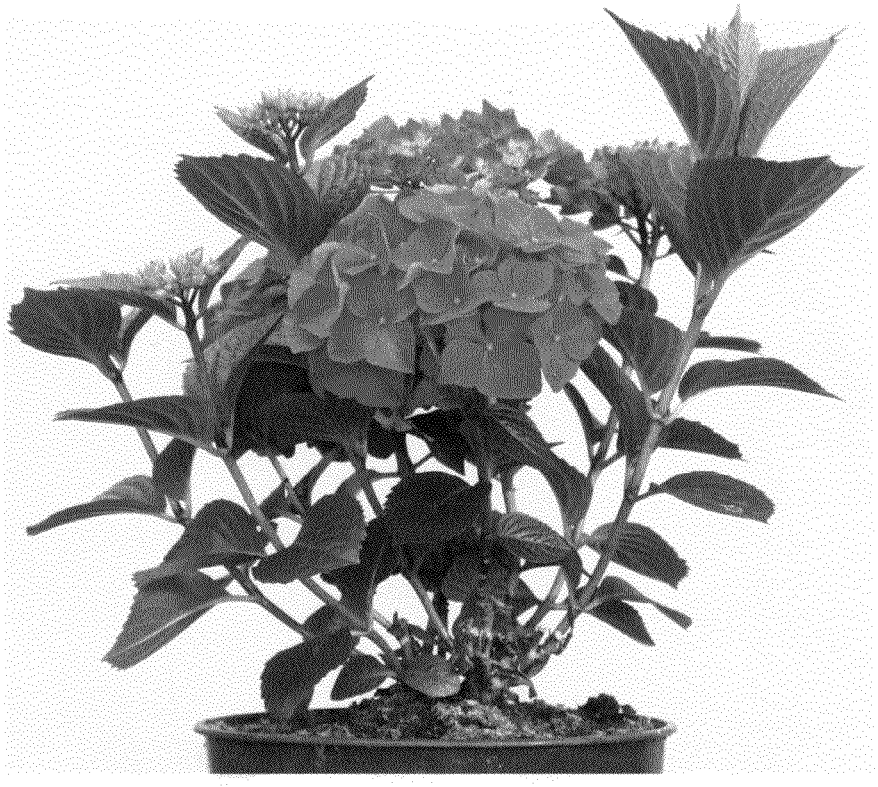

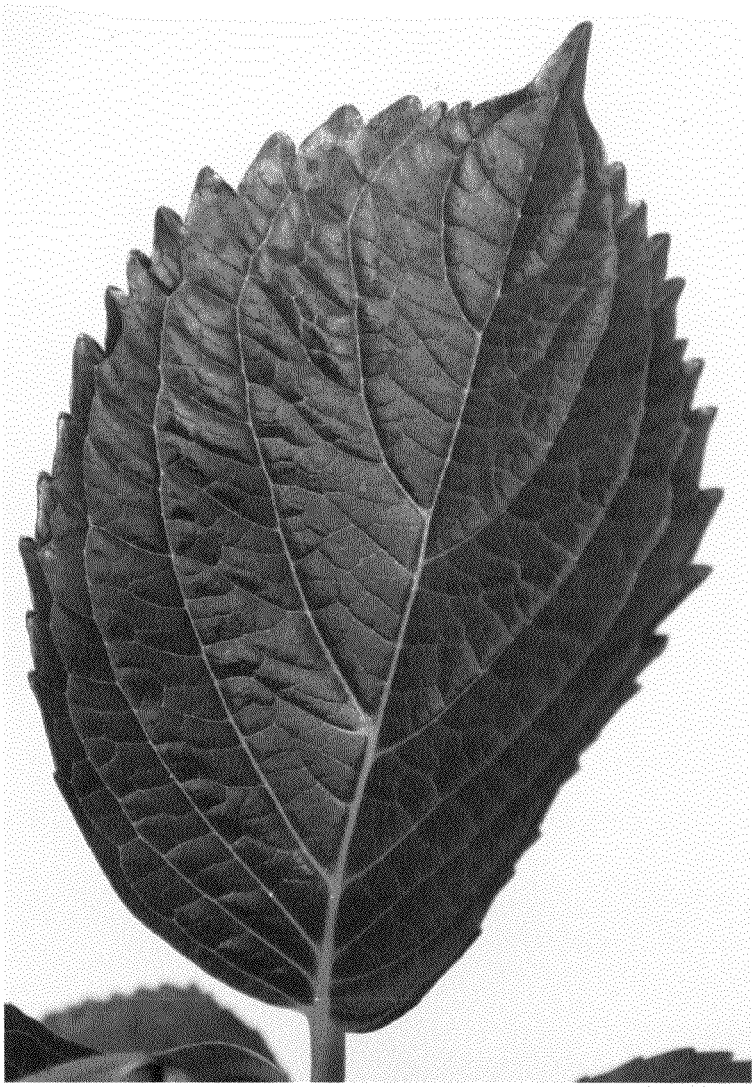

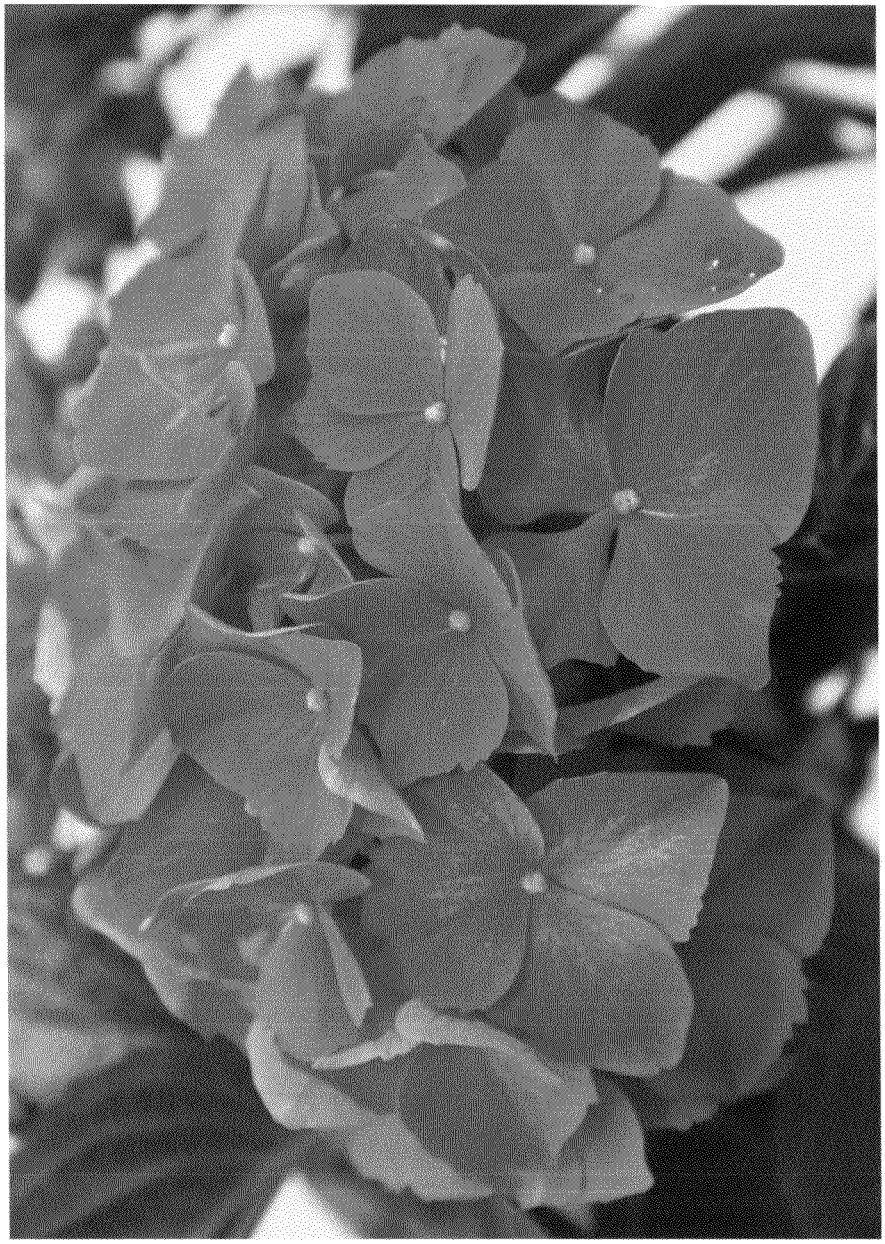

* * * * *